US010800799B2

(12) United States Patent  
Iraneta et al.

(10) Patent No.: US 10,800,799 B2  
(45) Date of Patent: Oct. 13, 2020

(54) METHODS, COMPOSITIONS, DEVICES, AND KITS, FOR PERFORMING PHOSPHOLIPID SEPARATION

(71) Applicant: Waters Technologies Corporation, Milford, MA (US)

(72) Inventors: Pamela C. Iraneta, Brighton, MA (US); Thomas H. Walter, Ashland, MA (US); Xin Zhang, Natick, MA (US); Daniel P. Walsh, Danvers, MA (US); Kevin D. Wyndham, Upton, MA (US); Raymond P. Fisk, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 333 days.

(21) Appl. No.: 15/941,338

(22) Filed: Mar. 30, 2018

(65) Prior Publication Data

US 2018/0291044 A1 Oct. 11, 2018

Related U.S. Application Data

(63) Continuation of application No. 13/580,884, filed as application No. PCT/US2011/037438 on May 20, 2011, now Pat. No. 9,951,092.

(Continued)

(51) Int. Cl.
*B01D 15/00* (2006.01)
*B01J 20/00* (2006.01)
(Continued)

(52) U.S. Cl.
CPC .............. *C07F 9/103* (2013.01); *B01D 15/22* (2013.01); *B01D 15/327* (2013.01);
(Continued)

(58) Field of Classification Search
CPC ........... B01J 20/281; G01N 2030/8813; G01N 1/405; G01N 1/34; G01N 30/88; C07F 9/103
See application file for complete search history.

(56) References Cited

U.S. PATENT DOCUMENTS

2005/0054077 A1   3/2005  Bennett et al.
2008/0213906 A1   9/2008  Aurand et al.
(Continued)

FOREIGN PATENT DOCUMENTS

EP      0298062 A1   1/1989
WO   2011017418 A1   2/2011

OTHER PUBLICATIONS

Applied Porous Technology website, "WHITE PAPER: Metal filter products and the LC system." Mar. 20, 2008. obtained by the examiner from the Web Archive at address <http://http://web.archive.org/web/20080320040858/http://www.appliedporous.com/frits-chromatography.htm> on Feb. 29, 2016.

(Continued)

*Primary Examiner* — Christopher Adam Hixson
(74) *Attorney, Agent, or Firm* — Womble Bond Dickinson (US) LLP; Deborah M. Vernon; Benedict L. Hanrahan

(57) ABSTRACT

Methods, kits and devices for separating phospholipids and proteins from small molecules in biochemical samples can feature an apparatus having a wetting barrier, at least one frit and a separation media. For example, an apparatus can include at least one wall defining a chamber having an exit and an entrance; a wetting barrier disposed between the exit and entrance, so as to define a separation media space located between the wetting barrier and the exit and a sample receiving area located between the wetting barrier and the (Continued)

entrance; and a separation media disposed adjacent to the wetting barrier and having a specific affinity for phospholipids.

22 Claims, 4 Drawing Sheets

Related U.S. Application Data

(60) Provisional application No. 61/346,639, filed on May 20, 2010.

(51) Int. Cl.

| | |
|---|---|
| *G01N 1/00* | (2006.01) |
| *C07F 9/10* | (2006.01) |
| *B01D 15/32* | (2006.01) |
| *B01J 20/28* | (2006.01) |
| *B01J 20/287* | (2006.01) |
| *B01J 20/32* | (2006.01) |
| *B01J 20/10* | (2006.01) |
| *B01D 15/22* | (2006.01) |
| *B01L 3/00* | (2006.01) |
| *C07K 1/30* | (2006.01) |
| *G01N 30/88* | (2006.01) |

(52) U.S. Cl.
CPC ....... *B01J 20/103* (2013.01); *B01J 20/28004* (2013.01); *B01J 20/287* (2013.01); *B01J 20/28019* (2013.01); *B01J 20/28061* (2013.01); *B01J 20/28069* (2013.01); *B01J 20/3204* (2013.01); *B01J 20/3217* (2013.01); *B01J 20/3246* (2013.01); *B01J 20/3293* (2013.01); *B01L 3/5023* (2013.01); *B01L 3/50255* (2013.01); *C07K 1/30* (2013.01); *B01J 2220/64* (2013.01); *B01L 2300/0681* (2013.01); *G01N 2030/8813* (2013.01)

(56) References Cited

U.S. PATENT DOCUMENTS

| | | |
|---|---|---|
| 2008/0287661 A1 | 11/2008 | Jones |
| 2011/0313143 A1 | 12/2011 | Martin et al. |

OTHER PUBLICATIONS

Extended European search report for EP Application No. 17180827.2, dated Oct. 11, 2017.
Hansen, Richard L., et al. "Lateral Diffusion of Molecules Partitioned into Silica-Bound Alkyl Chains: Influence of Chain Length and Bonding Density", Analytical Chemistry, Jan. 1, 1996, pp. 2879-2884, vol. 68, No. 17 US.
International Search Report and Written Opinion for International application No. PCT/US2011/037438, 2 pp. dated Aug. 24, 2011.
Kimata, Kazuhiro et al. Abstract of "Chromatographic characterization of silica C18 packing materials. Correlation between a preparation method and retention behavior of stationary phase." J. Chromat. Sci (1989) 27 721-728.
Lork, K.D., et al., "Solute Retention in Reversed-Phase Chromatography as a Function of Stationary Phase Properties: Effect of n-Alkyl Chain Length and Ligand Density", Chromatographia, Dec. 1, 1988, pp. 115-119, vol. 26, No. 1, DE.
Miller, Mark L., et al., "Correlation of Retention Behavior with Quantitative Surface Analysis of Octadecyl Bonded Chromatographic Supports", Oct. 1, 1984, pp. 2204-2210, vol. 56, No. 12, US.
Pucci V, et al.: A Novel strategy for reducing phospholipids-based batrix effect in LC-ESI-MS bionalysis by means of HybridSPE Journal of Pharmaceutical and Biomedical Analysis, NY—Dec. 5, 2009, pp. 867-871 vol. 50, No. 5.
Simko, Steven J., et al., "Quantitative Fast Atom Bombardment Mass Spectrometry of Silylated Silica Surfaces", Analytical Chemistry, Jan. 1, 1985, pp. 2448-2451, vol. 5713, No. 57.
Sunseri, David J., et al., "Complete Methylation of Silica Surfaces: Next Generation of Reversed-Phase Liquid Chromatography Stationary Phases, Langmuir", Jun. 10, 2003, pp. 8608-8610, vol. 19, No. 20, US.

METHODS, COMPOSITIONS, DEVICES, AND KITS, FOR PERFORMING PHOSPHOLIPID SEPARATION

CROSS-REFERENCE TO RELATED APPLICATIONS

This application is a continuation application U.S. Utility patent application Ser. No. 13/580,884 entitled "Methods, Compositions, Devices, and Kits for Performing Phospholipid Separation" which is a U.S. National Stage Entry of PCT/US11/37438, filed May 20, 2011, which claims priority from U.S. Provisional Patent Application 61/346,639, filed May 20, 2010.

FIELD OF THE INVENTION

The invention is directed to devices and methods for performing chromatography. More particularly, embodiments of the invention feature devices and methods for separating phospholipids from other constituents of a sample.

BACKGROUND OF THE INVENTION

Many biological samples (e.g., in clinical, diagnostic, and research settings) include matrix compounds such as proteins, peptides, and phospholipids. Such samples include, for example, plasma, sera, secretions, body fluids, cells, and tissues. However, in a broader sense, a sample can include any mixture which an individual desires to separate or analyze. A mixture can be a fluid (e.g., including water and/or other liquids and gases) including one or more dissolved or suspended compounds (e.g., a compound of interest or an analyte). To study and/or analyze such samples, at least one matrix compound can be separated, removed, concentrated, and/or isolated. Such methods of separating, removing, concentrating, and/or isolating one or more compounds found in a mixture or sample are generally known as chromatography.

Chromatography can separate, remove, concentrate, and/or isolate a compound based upon a difference between the compound's affinity for the sample and the compound's affinity for a second phase (e.g., chromatography media). Chromatography can be facilitated by the relative movement of the sample and the second phase. For example, the mixture (e.g., a mobile phase) is generally moved in relation to a packed bed of particles or a porous monolith structure (e.g., a stationary phase).

Samples from biological sources such as blood, plasma, tissues, secretions, and the like often include combinations of various proteins, peptides, and/or phospholipids. Such samples can also include smaller molecules and/or other compounds of interest. Proteins and peptides are polymers of amino acids and are often present in samples. Phospholipids are class of lipids that contain a phosphate functional group and a more hydrophobic functional group. Another class of lipids, glycerophospholipids, contains one or two long saturated and/or unsaturated hydrocarbon tails attached to a glycerol residue which contains at the C-1 position a derivatized phosphoric acid polar head group. The composition of the polar head group is a phosphoric acid group derivatized by choline, serine, or ethanolamine to form phosphatidylcholine, phosphatidylserine, or phosphatidylethanolamine lipids, respectively. Smaller molecules (e.g., small organic molecule such as drugs or drug candidates) can have a wide range of chemical and physical properties. The broad differences in chemical and physical properties between mixtures of such components can present a chromatographic challenge.

SUMMARY OF THE INVENTION

Embodiments of the invention feature media, methods, devices, and kits for phospholipid separation. For example, the invention can be used to separate phospholipids from other constituents of a sample. Other sample constituents can include proteins, peptides, nucleic acids, oligonucleotides, and/or other compounds of interest such as organic molecules, known drug compounds, prospective drug compounds, lipids, sugars, carbohydrates, other biomolecules and biopolymers, and the like.

One embodiment is directed to a device for performing separations of proteins and phospholipids potentially held in solution or suspension in a fluid sample to allow analysis of the small molecule analytes. The device includes the following elements: a housing, at least one wetting barrier, a separation media, and at least one first frit. The housing has at least one wall defining a chamber having an exit opening and an entrance opening. The at least one wetting barrier element is positioned in the chamber to define a separation media space in the chamber proximal to the exit opening and a sample receiving area proximal to the entrance opening. The sample receiving area is for receiving at least one sample and at least one protein precipitating agent. The at least one wetting barrier element is for holding at least one sample, at least one protein precipitating agent and one or more precipitated proteins in the sample receiving area and releasing and forming a processed sample. Upon the application of a differential gas pressure across the chamber of greater than 4" Hg, or a centrifugal force equivalent thereto, the processed sample is released to the separation media. The separation media is held in the separation space of the chamber. The separation media has specific affinity for phospholipids. The at least one first frit is incorporated and part of the at least one wetting element or has a position between the separation media and the entrance opening. The at least one first frit has a plurality of first frit openings having a size to retain the protein precipitant, to allow said frit in combination of the wetting barrier element to retain protein precipitant upon the application of a pressure differential of at least 20" Hg, or a centrifugal force equivalent thereto, to the chamber. The device is adapted to receive a sample and at least one protein precipitating agent in the sample receiving area, form precipitated proteins if proteins are present in the sample receiving area, collect precipitated protein on the frit upon the application of a differential gas pressure of greater than 4" Hg across the chamber, or a centrifugal force equivalent thereto, and retain phospholipids on said separation media allowing small molecules to elute through the exit opening.

In various embodiments, specific affinity for phospholipids is reflected in the realization of a high retention of phospholipids (e.g., >85%, >90%, >95%). In various embodiments, specific affinity for phospholipids results from the phospholipids interacting with the separation media by way of at least two simultaneous specific types of interactions. The two types of interacting groups on the separation media can include, but are not limited to, (i) silanol groups or other polar groups and (ii) C18 groups or other hydrophobic groups. A combination of these two simultaneous specific types of interactions can enhance phospholipids retention, over that for similar non-polar molecules having non-phospholipid-like structures.

In various embodiments, the wetting barrier is adapted to (i) retain a liquid sample under a first force and (ii) flow the sample through the wetting barrier under a second force, wherein the second force is greater than the first force. The exact force will vary based upon a number of factors including, the sample solvent and composition, the wetting barrier material, and the apparatus configuration (e.g., the wetting barrier surface area in the sample receiving area). In various embodiments, the wetting barrier can be a porous element that exhibits a contact angle of greater than 90° (non-wetting) with the sample and a mixture of sample and acetonitrile containing at least 75% acetonitrile by volume. The pore size of the porous element is selected to retain the sample mixture above the separation media, preventing penetration, until a differential gas pressure of greater than 4" Hg, or a centrifugal force equivalent thereto, is applied to the fluid. For the examples described herein, this force is generally equal to about 2.5 lbs/in$^2$.

In some embodiments, the frit openings are selected to cooperate with the formation of the protein precipitant and the conditions for forming the protein precipitant. Large protein precipitants can be favored by gentle mixing and/or longer reaction times. Example devices can feature a first frit and the at least one wetting barrier element having openings of about five to five hundred microns, or ten to one hundred microns. As used herein the term retain, such as to retain protein precipitants and phospholipids, is not necessarily absolute (e.g., 100% retention). The term can be used, for example, to denote retention of 50%, or 75%, or preferably 90% of the protein precipitant and or phospholipids. Other examples include 55, 65, 70, 80, 85, 86, 87, 88, 89, 91, 92, 93, 94, 95, 96, 97, 98, or 99% retention.

One aspect of the device of features at least one wetting barrier element that is a fluorocarbon polymer coating on the first frit. Another aspect of the device features the at least one wetting barrier element selected from the group of frits, perforated sheets, screens, membranes, fabrics and filters. Another aspect of the device is directed to the at least one wetting barrier element having a surface for being placed in contact with said sample in which the surface is hydrophobic and, optionally, also having a pore size that in combination with the contact angle and surface tension prevents penetration of the separation media by the sample mixture containing at least 75% acetonitrile by volume. One such hydrophobic surface is a fluorocarbon polymer. The fluoropolymer surface may be carried or present throughout the wetting barrier element or be present as a coating.

One aspect of the present device further comprising a second frit positioned proximal the exit opening. The second frit holds the separation media in the chamber. A second frit can include, for example, one or more frits, membranes, perforated sheets, screens, filters, and their equivalents.

Embodiments of the present device can present a single chamber or the housing has a plurality of chambers. One aspect of the present invention features a housing constructed and arranged to have 96 chambers or other multiples of 8 chambers. The device is constructed and arranged to present the chambers in a plate-like format.

One aspect of the present device features a cap (e.g., for closing the chamber after the chamber receives a sample). In one aspect the cap is constructed and arranged to receive a fluid pressure source to create a pressure differential across the chamber (e.g., a positive pressure, applied at the chamber entrance). In another aspect, the cap is constructed and arranged to support the application of a negative fluid pressure, to create a pressure differential across the chamber (e.g., a negative pressure, or suction, applied at the chamber exit). In one aspect the device is constructed and arranged to have a single chamber and a single cap, or multiple chambers in a single housing and a plurality of caps, or multiple chambers in a single housing and multiple cap elements in a single cap piece in which the cap elements are arranged to cooperate with the chambers.

One aspect of the present device is housing is constructed and arranged to fit a centrifuge. The device presents a housing with a single chamber. Another aspect of the present invention is a device constructed and arranged to cooperate with a vacuum source to empty said chamber.

One aspect of the device is directed to a sorbent having a core composition and a surface composition represented by formula 1 below:

$$W\text{—}[X]\text{-}Q \qquad \text{Formula 1}$$

As used above, X represents the core composition and W and Q occupy free valences of the core or surface composition that are not X or W is hydrogen or a hydroxyl group and Q is selected from the group of hydrogen, hydroxyl, and aliphatic silane groups, such that W and Q form the surface composition.

A preferred X is a monolithic, spherical, granular, superficially porous, and irregular materials that are inorganic (silica, alumina, titania, zirconia) or hybrid inorganic/organic materials. Also included in this are materials that independently have an inorganic (silica, alumina, titania, zirconia) or hybrid inorganic/organic materials surface layer on a porous inorganic (silica, alumina, titania, zirconia) or hybrid inorganic/organic materials core material.

One aspect of the formula is wherein at least a fraction of Q is an aliphatic silane group. A preferred aliphatic group has six to 30 carbons; and in one aspect of the invention, the aliphatic group has eighteen carbons.

In one aspect, Q is selected from Z—R1 and Z—R2 in which R1 is a higher alkyl and R2 is a lower alkyl, and Z represents a silicon, siloxane, metal or metal oxide attachment to the core material X, and open valences of such Z are, hydrogen or hydroxyl, R1 or R2. As used herein, the term "lower alkyl" refers to carbon groups having one to ten carbons, and the term "higher alkyl" refers to carbon groups having ten to forty carbons.

A preferred Z is a silane. Preferably, the surface composition has a combined surface concentration of Si—R1 and Si—R2 of 0.40 to 3.2 micromoles per square meter. And, more preferably 0.5 to 2.7 micromoles per square meter, and still more preferably 0.6 to 2.2 micromoles per square meter.

In one aspect, W is selected to have at least one polar group and Q is selected to have at least one hydrophobic group. In one aspect, the polar groups and hydrophobic groups define a ratio of about greater than 25% or 50% or 90%. One example is where at least a fraction W is hydroxyl and hydroxyl on said surface composition and Q is an aliphatic group.

The polar group and hydrophobic group can also be defined as a ratio. One aspect of the invention is wherein the hydroxyl and aliphatic group have a concentration on said surface forming a ratio of concentration, the ratio of hydroxyl to combined Si—R1 and/or SiR2 being 2.0-26, 2.3-18, 3.5-14, 2.5-20 or 4.5-12.

One aspect of the device features a separation media in the form of particles or as a porous monolith material. In one aspect the particles have a diameter of 0.4-3.0 mm. In one aspect the separation media has a pore volume of 0.5-1.7 cm$^3$/g.

Embodiments of the present invention feature a method of separating of proteins and phospholipids potentially held in solution or suspension in a fluid sample to allow analysis of one or more small molecule analytes. The method has the steps of providing a device having a housing, at least one wetting barrier element, a separation media, and at least one first frit as described previously. The method has a step of combining a sample with protein precipitating agents in the sample receiving area to from a protein precipitant in the presence of proteins and a processed sample. Next, the processed sample is compelled though the wetting barrier element under the application of a differential gas pressure of greater than 4" Hg across the chamber, or a centrifugal force equivalent thereto. Phospholipids, potentially present in the processed sample are retained in the separation media and precipitated proteins are retained at or about the frit, the wetting barrier or separation media. Small molecules analytes are passed to the exit opening.

In aspects of the present method featuring a cap, the cap is placed over the chamber after the chamber receives the sample. One aspect features a cap for placing a pressure differential in the chamber in which the method comprises placing a pressure differential of 4" Hg between said sample receiving area and the separation media space through the cap.

In aspects of the invention that feature a housing constructed and arranged to fit a centrifuge, the method comprises the step of placing the housing in a centrifuge and activating the centrifuge to move the processed sample into and through said separation media.

In aspects of the invention that feature a housing is constructed and arranged to cooperate with a vacuum source to empty the chamber, the method comprises the step of placing the exit separation media space in communication with a vacuum source to create a pressure differential in said chamber.

The devices of the present invention are well suited for incorporation into kits. Kits are bundled assemblies which comprise components such as the device and/or one or more agents or reagents, such as by way of example, a protein precipitating reagent or agent, buffers and the like, with instructions for their use. The bundled assemblies are normally packaged as a single unit for use by the end user.

The invention includes an apparatus for separating a liquid sample potentially comprising one or more proteins, phospholipids, and small molecules. The apparatus includes (i) at least one wall defining a chamber having an exit and an entrance, (ii) a wetting barrier disposed between the exit and entrance, so as to define a separation media space located between the wetting barrier and the exit and a sample receiving area located between the wetting barrier and the entrance, and (iii) a separation media disposed adjacent to the wetting barrier and having a specific affinity for phospholipids. The wetting barrier is adapted to (i) retain the liquid sample and a protein precipitating agent in the sample receiving area under a first force, thereby facilitating the formation of a protein precipitate and a processed sample, and (ii) flow the processed sample through the wetting barrier and separation media under a second force, wherein the second force is greater than the first force, thereby retaining the protein precipitate in the sample receiving area, retaining phospholipids in the separation media, and eluting small molecules.

The invention includes a method for separating a liquid sample potentially comprising one or more proteins, phospholipids, and small molecules. The method includes providing (i) at least one wall defining a chamber having an exit and an entrance, (ii) a wetting barrier disposed between the exit and entrance, so as to define a separation media space located between the wetting barrier and the exit and a sample receiving area located between the wetting barrier and the entrance, and (iii) a separation media disposed adjacent to the wetting barrier and having a specific affinity for phospholipids. Further, the method includes contacting the liquid sample and a protein precipitating agent in the sample receiving area under a first force, thereby forming a protein precipitate and a processed sample. Furthermore, the method includes flowing the processed sample through the wetting barrier and separation media under a second force, wherein the second force is greater than the first force, thereby retaining at least a fraction of the protein precipitate in the sample receiving area, retaining phospholipids in the separation media, and eluting small molecules.

In various embodiments, the second force is a fluid pressure differential of greater than 4" Hg across the chamber, or a centrifugal force effectively equivalent thereto.

In some embodiments, the apparatus includes a first frit integral to the wetting barrier or disposed between the separation media and the entrance, wherein the first frit comprises a plurality of openings adapted to retain the protein precipitant in the sample receiving area under a third force, wherein the third force is greater than the second force. A method can include providing such a frit. The third force can be a fluid pressure differential of at least 20" Hg across the chamber, or a centrifugal force effectively equivalent thereto.

In certain embodiments, retaining the phospholipids comprises retaining at least 85%, at least 90%, or at least 95% of the phospholipids in the separation media.

It is understood by those skilled in the art that the various aspects and features described herein can be adapted and combined with the various embodiments of the invention. These and other features and advantages will be apparent to those skilled in the art upon reading the detailed description that follows and viewing the drawings which are briefly described below.

DETAILED DESCRIPTION OF THE INVENTION

The invention will now be described in detail with respect to the preferred embodiments and the best mode in which to make and use the invention. Those skilled in the art will recognize that the embodiments described are capable of being modified and altered without departing from the teachings herein.

Figure 1:
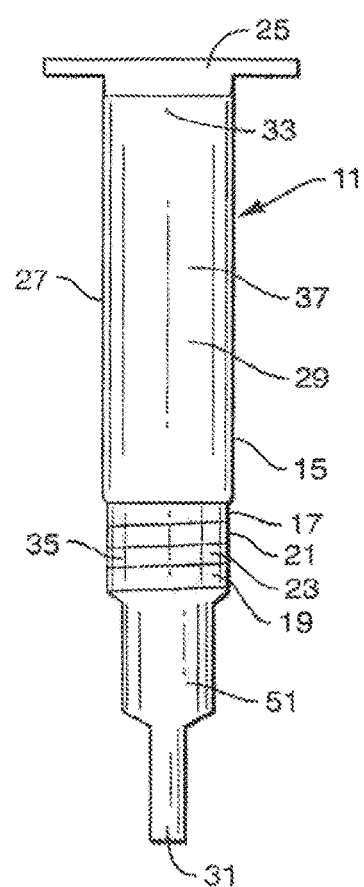
FIG. 1 depicts in cross section a device embodying features of the present invention.

Turning now to FIG. 1, a device embodying features of the present invention, generally designated by the numeral 11, is depicted in cross-section. Device 11 can perform separations of proteins and phospholipids potentially held in solution or suspension in a fluid sample, to allow analysis of the small molecule analytes. The device 11 includes the following elements: a housing 15, a first frit element 17, a second frit element 19, a wetting barrier element 21, a separation media 23 and a cap element 25. In general, the invention can be used to separate phospholipids from other sample constituents. Other sample constituents can include proteins, peptides, nucleic acids, oligonucleotides, and/or other compounds of interest such as organic molecules, known drug compounds, prospective drug compounds, lipids, sugars, carbohydrates, and other biopolymers.

Figure 2:
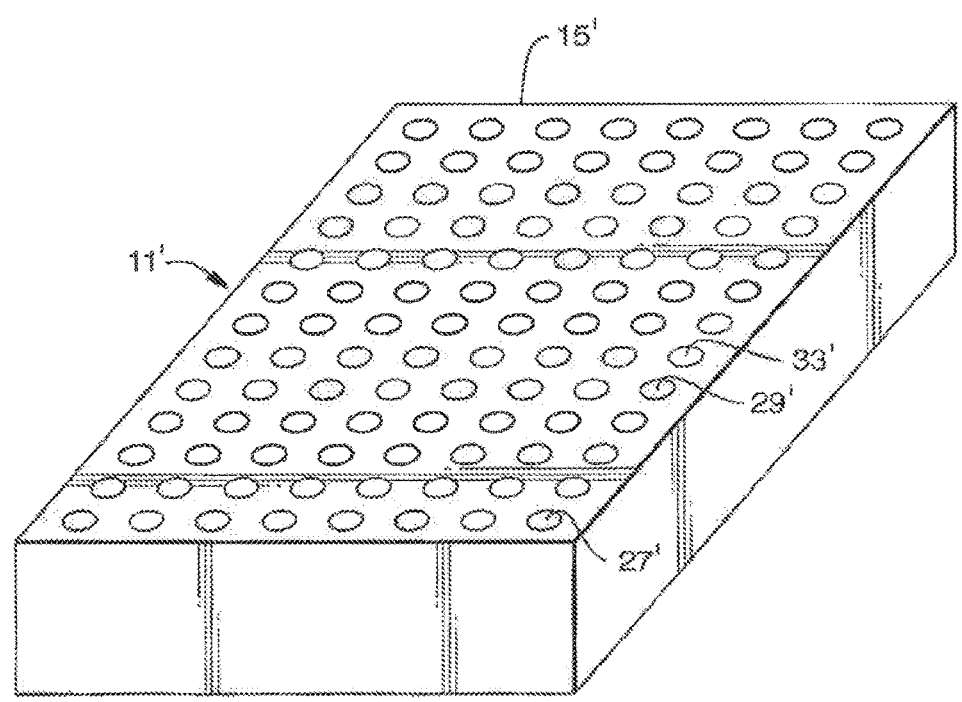
FIG. 2 depicts a device embodying features of the present invention.

The housing 15 includes at least one wall 27 defining a chamber 29, an exit opening 31, and an entrance opening 33. The housing 15 is depicted in FIG. 1 in which the at least one wall defines a single chamber 29. FIG. 2 depicts a device 11' having at least one wall 27' that defines a housing 15' having a plurality of chambers 29'. These chambers 29' are constructed and arranged in a 96 well plate format. However, those skilled in the art will recognize that any number of chambers 29' may be defined by wall 29'. The number of chambers can be 96 or another multiple of 8. Other multiples are possible and can be selected based upon a user's requirements.

The discussion that follows with respect to FIG. 1 applies as well to FIG. 2 where the multiplicity of chambers 29' does not permit the same degree of detail. Referring now to FIG. 1, housing 15 is formed of a substantially rigid material such as a glass, metal, and/or plastic. Moldable plastics, such as PEEK, are known in the art.

The device 11 has at least one wetting barrier element 21 positioned in the chamber 29 to define a separation media space 35 in the chamber 29 proximal to the exit opening 31 and a sample receiving area 37 proximal to the entrance opening 33. The sample receiving area 37 is adapted to receive at least one sample and at least one protein precipitating agent [not shown in FIGS. 1 and 2]. The at least one wetting barrier element 21 adapted to hold at least one sample, at least one protein precipitating agent, and one or more precipitated proteins in the sample receiving area 37, thereby facilitating the formation of a processed sample. The processed sample can be a sample in which the proteins held in solution and/or in suspension are in whole or in part forming and/or have formed a protein precipitant.

In various embodiments, the wetting barrier is adapted to (i) retain a liquid sample under a first force and (ii) flow the sample through the wetting barrier under a second force, wherein the second force is greater than the first force. The exact force will vary based upon a number of factors including, the sample solvent and composition, the wetting barrier material, and the apparatus configuration (e.g., the wetting barrier surface area in the sample receiving area). In various embodiments, the wetting barrier can be a porous element that exhibits a contact angle of greater than 90° (non-wetting) with the sample and a mixture of sample and acetonitrile containing at least 75% acetonitrile by volume. The pore size of the porous element is selected to retain the sample mixture above the separation media, preventing penetration, until a differential gas pressure of greater than 4" Hg, or a centrifugal force equivalent thereto, is applied to the fluid. For the examples described herein, this force can be equal to about 2.5 lbs/in$^2$.

For example, the wetting barrier element 21 holds the sample, one or more protein precipitating agents, protein precipitants, and processed sample by resisting flow by surface tension, pore size, and/or contact angle. Upon the application of a differential gas pressure of greater than 4" Hg across the chamber 29, or a centrifugal force equivalent thereto, the processed sample is released to the separation media 23.

The wetting barrier element 21 can be selected from the group of porous or open structures such as frits, screens, membranes, perforated sheet, fabrics, filters, packed bed and the like. A preferred wetting barrier element 21 is formed of or has a surface of a fluorocarbon polymer. Fluorocarbon polymers are known in the art and are commercially available under a variety of trademarks such as Teflon® (DuPont, Del., USA). For example, without limitation, the wetting barrier 21 may comprise a packed bed of fluorocarbon polymer coated beads or particles, or beads and particles formed of a fluorocarbon polymer, a screen, frit, membrane, perforated sheet, fabric, filter or the like coated with or formed with a fluorocarbon polymer. Screens, frits, membranes, perforated sheets, fabrics, filters are preferably made of metals (e.g., stainless steel), plastics, and silicates.

The separation media 23 is held in the separation space 35 of the chamber 29. The separation media 23 has specific affinity for phospholipids. The separation media 23 can also exhibit a non-specific affinity for proteins and/or can physically retain protein precipitants.

In various embodiments, specific affinity for phospholipids is reflected in the realization of a high retention of phospholipids (e.g., >85%, >90%, >95%). In various embodiments, specific affinity for phospholipids results from the phospholipids interacting with the separation media by way of at least two simultaneous specific types of interactions. The two types of interacting groups on the separation media can include, but are not limited to, (i) silanol groups or other polar groups and (ii) C18 groups or other hydrophobic groups. A combination of these two simultaneous specific types of interactions can enhance phospholipids retention, over that for similar non-polar molecules having non-phospholipid-like structures.

The separation media 23 is held between the wetting barrier element 21 and the second frit 19. The second frit 19 maintains the bed integrity of the separation media 23 where the separation media 23 is particulate. In embodiments where the separation media 23 is a porous monolith material, or a similar material that does not require the support of a second frit 19, the second frit 19 is not required.

The at least one first frit 17 is depicted on top of the wetting barrier element 21. In various embodiments, the first frit 17 can be used to maintain the position of the wetting barrier element 21. However, the relative positions of the first frit 17 and wetting barrier element 21 can be switched. In other embodiments, the at least one wetting element also functions as the at least one first frit, or the at least one first frit is incorporated and part of the at least one wetting element 21. For example, the at least one first frit 17 may be coated with a fluorocarbon polymer. In such embodiments, a separate first frit is not required.

The at least one first frit 17 and/or the wetting barrier element 21 can have a plurality of openings [not shown] having a size adapted to retain the protein precipitant. More particularly, the at least one first frit 17 in combination with the wetting barrier element 21 can be adapted to retain protein precipitant upon the application of a pressure differential of at least 20" Hg, or a centrifugal force equivalent thereto, to the chamber 29. The first frit 17 openings are selected to cooperate with the formation of the protein precipitant and the conditions for forming the protein precipitant. For example, if the pores are too small then the precipitated will plug the first frit and the sample will not be able to flow. On the other hand, if the pores are too large then the precipitate will flow to, and plug, the wetting barrier. Thus, the size of the pores can be selected based on the size of the precipitates that the user wishes to retain. The user also has a degree of control over the size of the precipitate.

For example, larger protein precipitants can be favored by gentle mixing and longer reaction times.

One device features a first frit 17 and the at least one wetting barrier element 21 having openings of about five to five hundred microns, or more preferably, ten to one hundred microns. As used herein the term retain, such as to retain protein precipitants and phospholipids, is not necessarily absolute (e.g., 100% retention). The term can be used, for example, to denote retention of 50%, or 75%, or preferably 90% of the protein precipitant and or phospholipids. Other examples include 55, 65, 70, 80, 85, 86, 87, 88, 89, 91, 92, 93, 94, 95, 96, 97, 98, or 99% retention.

One embodiment features a second frit 19 with similar or identical sized openings [not shown] to that of the wetting barrier element 21 and the at least one first frit 17, to remove protein precipitants. The second frit 19 is positioned proximal the exit opening 31. The second frit 19 can include one or more frits, membranes, perforated sheets, screens, filters and their equivalents.

A third frit [not shown] can be interposed between the wetting element 21 and the separation media 23, for example, to limit movement of the wetting barrier element 21. The third frit [not shown] is preferably identical or similar to the at least one first frit 17, to allow the first frit 17, wetting barrier element 21, and third frit [not shown] to form an assembly which can be placed in the chamber 29 without reference to order. Such an assembly is essentially non-directional (e.g., asymmetric in that the top and bottom faces are essentially the same), which facilitates assembly because the orientation of the assembly does not need to be controlled as it it inserted into the chamber.

The device 11 can receive a sample and at least one protein precipitating agent in the sample receiving area 37, form precipitated proteins if proteins are present in the sample receiving area 37, collect precipitated protein on the at least one first frit 17 upon the application of a differential gas pressure of greater than 4" Hg across the chamber 29, or a centrifugal force equivalent thereto, and retain phospholipids on the separation media 23, allowing small molecules to elute through the exit opening 31.

FIG. 1 depicts a device 11 having a cap 25 for closing the chamber 29 after the chamber 29 receives a sample. In one aspect, the cap 25 is constructed and arranged to receive a fluid pressure source [not shown] to create a pressure differential in the chamber. For example, one embodiment features a cap 25 having a porous mat though which gas such as atmospheric air may be received. The housing 15 is placed in a manifold in association with the pressure source to pressurize the sample receiving section 37 of chamber 29 driving fluid through the wetting barrier element 21. In the alternative, the cap 25 has a hose connection [not shown] for being placed in communication with a pressure source. In the alternative, housing 15 is placed in a manifold in association with a vacuum source and a pressure differential is created by vacuum through the exit opening 31.

As depicted in FIG. 1, example device 11 is constructed and arranged to have a single chamber 29 and a single cap. In FIG. 2, example devices 11' having multiple chambers 29 in a single housing 15 can have a plurality of caps [not shown], or a single or group cap housing [not shown] having multiple cap elements in a single cap piece arranged to cooperate with the chambers 29'.

Returning now to FIG. 1, the device 11 has a housing 15 constructed and arranged to fit a centrifuge. Housing 15 has a generally cylindrical shape which has a diameter of approximately 0.5 to 2.0 centimeter and a length of 4.0 to 20 centimeters, to cooperate with conventional opening for vials and the like in centrifuges. However, other shapes, sizes, and configurations can be used. The area below the second frit 19, designated holding area 51, can collect a sample after it flows through the at least one first frit 17, wetting barrier element 21, separation media 23, and second frit 19.

The separation media 23 can be a sorbent having a core composition and a surface composition represented by formula 1 below:

Formula 1

As used above, X represents the core composition and W and Q occupy free valences of the core or surface composition that are not X. W is hydrogen or a hydroxyl group and Q is selected from the group of hydrogen, hydroxyl, and aliphatic silane groups, such that W and Q form the surface composition.

In various embodiments, at least a fraction of Q can be an aliphatic silane group. A preferred aliphatic group has six to 30 carbons. In one example, the aliphatic group has eighteen carbons.

In some embodiments, Q is selected from Z—R1 and Z—R2 in which R1 is a higher alkyl and R2 is a lower alkyl, and Z represents a silicon, siloxane, metal or metal oxide attachment to the core material X, and open valences of such Z are, hydrogen or hydroxyl, R1 or R2. As used herein, the term "lower alkyl" refers to carbon groups having one to ten carbons, and the term "higher alkyl" refers to carbon groups having ten to forty carbons.

In some embodiments, W is selected to have at least one polar group and Q is selected to have at least one hydrophobic group. In one aspect, the polar groups and hydrophobic groups define a ratio of about greater than 25% or 50% or 90%. In certain embodiments, the polar group to hydrophobic group ratio can be 0.20, 0.25, 0.30, 0.35, 0.40, 0.45, 0.50, 0.55, 0.60, 0.65, 0.70, 0.75, 0.80, 0.85, 0.90, or 0.95. In one example, at least a fraction of W is hydroxyl and Q is an aliphatic group.

The polar group and hydrophobic group can also be defined as a ratio. One aspect of the invention is wherein the hydroxyl and aliphatic group have a concentration on said surface forming a ratio of concentration, the ratio of hydroxyl to combined Si—R1 and/or SiR2 being 2.0-26, 2.3-18, 3.5-14, 2.5-20 or 4.5-12.

One aspect of the device features a separation media in the form of particles or as a porous monolith material. In one aspect the particles have a diameter of 0.4-3.0 mm. In one aspect the separation media has a pore volume of 0.5 to 1.7 $cm^3/g$.

The operation of the present invention and how to use the device 11 will now be described with respect to a method of separating of proteins and phospholipids potentially held in solution or suspension in a fluid sample to allow analysis of one or more small molecule analytes. Referring now to FIG. 1, the method has the steps of providing a device 11 having a housing 15, at least one wetting barrier element 21, a separation media 23, and at least one first frit 17 as described previously. A sample is combined with protein precipitating agents in the sample receiving area 37 to from a protein precipitant in the presence of proteins and a processed sample. Next, the processed sample is compelled though the wetting barrier element 21 under a pressure differential of greater than 4" Hg or a centrifugal force equivalent thereto. Phospholipids potentially present in the processed sample are retained in the separation media 23 and any precipitated proteins are retained at or about the at least one first frit 17, the wetting barrier element 21, or separation media 23.

Small molecules analytes, if present, are passed to the exit opening 31 in a finished sample.

In various embodiments, a cap 25 is placed over the chamber 29 after the chamber 29 receives the sample. The cap 25 can be adapted for supporting a pressure differential across the chamber of greater than 4" Hg between said sample receiving area 37 and the separation media space 23. The pressure differential can be created by applying positive pressure through the cap 25, or by applying a vacuum through exit opening 31.

In aspects of the invention that feature a housing 15 constructed and arranged to fit a centrifuge, the method can comprise the step of placing the housing 15 in a centrifuge and/or activating the centrifuge to move the processed sample into and through said separation media 23. The force applied to the sample by the centrifuge can be a centrifugal force effectively equivalent to a pressure difference of greater than 4" Hg across the chamber (e.g., a force sufficient to flow a sample through the wetting barrier).

Figure 3:
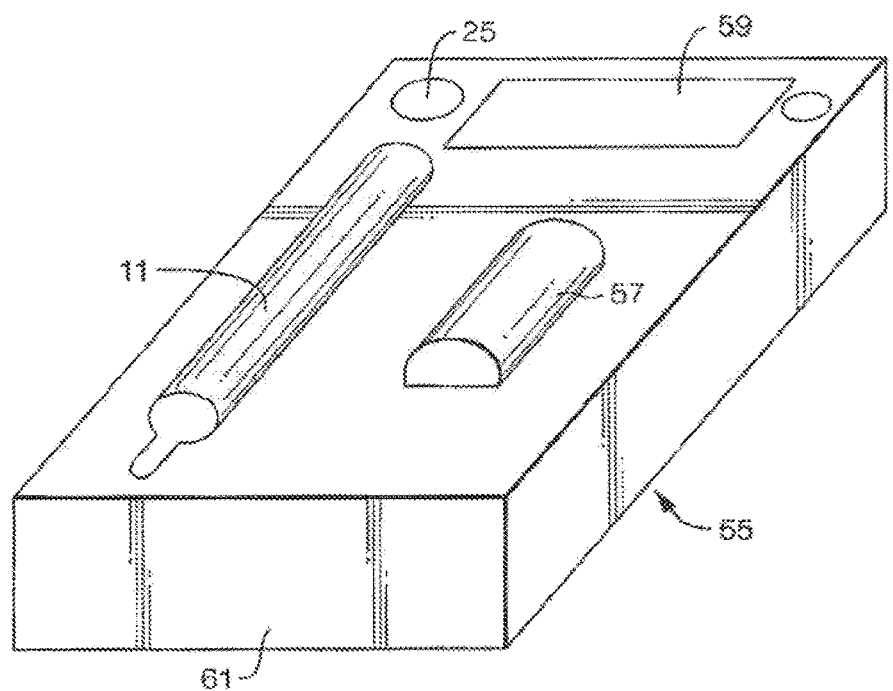
FIG. 3 depicts a kit embodying features of the present invention.

Devices according to the invention are well suited for incorporation into kits. In general, kits can include bundled components such as a device and/or one or more agents or reagents (e.g., a protein precipitating reagent or agent, buffers, and the like) and/or instructions for use. An exemplary kit 55, is depicted in FIG. 3. The kit 55 comprises a device 11, cap 25, one or more vials of protein precipitating reagent of which only one is depicted bearing a numeral 57, instructions 59 for the use of the device 11, cap 25 and vial 57, packaged as a single unit in a box 61, package, wrap, bag or other means [not shown] for use by the end user. In general, kits can include essentially any combination of these or other components discussed herein, for use or sale.

EXAMPLES

Protocols: The present invention is further illustrated by the following non-limiting protocols describing, among other things, the surface modification of porous chromatographic materials.

Materials: All reagents were used as received unless otherwise noted. Those skilled in the art will recognize that equivalents of the following supplies and suppliers exist and, as such, the suppliers listed below are not to be construed as limiting.

Physical Characterization: Those skilled in the art will recognize that equivalents of the following instruments and suppliers exist and, as such, the instruments listed below are not to be construed as limiting.

The % C values were measured by Coulometric Carbon Analyzer (modules CM5300, CM5014, UIC Inc., Joliet, Ill.) or an equivalent analyzer. The specific surface areas (SSA), specific pore volumes (SPV) and the average pore diameters (APD) of these materials were measured using the multi-point N2 sorption method (Micromeritics ASAP 2400; Micromeritics Instruments Inc., Norcross, Ga.). The SSA was calculated using the BET method, the SPV was the single point value determined for P/P0>0.98 and the APD was calculated from the desorption leg of the isotherm using the BJH method. Particle sizes were measured using a Beckman Coulter Multisizer 3 analyzer (Miami, Fla.). The particle diameter (dp) was measured as the 50% cumulative diameter of the volume based particle size distribution. The silanol concentration on silica was determined by weight loss measured using a Perkin-Elmer TGA 7 thermogravimetric analyzer with a Perkin-Elmer TAC 7/DX thermal analysis controller (Waltham, Mass.) in the 185-1000° C. temperature range and SSA.

Protein Precipitation Chemicals and Procedure: A rat plasma (Equitech-Bio Inc., Kerrville Tex.) sample was spiked with 9 analytes, to the concentrations given in Table 1. Analytes were purchased from Sigma Aldrich (St Louis, Mo.), except for caffeine (Alfa aesar, Ward Hill, Mass.). Formic acid was purchased from J. T. Baker, Phillipsburg, N.J. Acetonitrile and methanol were purchased from Fisher, Fair Lawn, N.J.

TABLE 1

| Compounds | Desired conc. (µg/mL) |
| --- | --- |
| N-acetylprocainamide (tertiary amine) | 5 |
| Ketoprofen (acid) | 10 |
| Pyrenesulfonic acid (strong acid) | 10 |
| Caffeine (neutral) | 10 |
| Naphthalene sulfonic acid (strong acid) | 25 |
| Naproxen (weak acid) | 25 |
| Niflumic acid (zwitterion) | 10 |
| Propranolol (secondary amine) | 50 |
| Salicylic acid (acid) | 100 |

For 1 cc cartridges, the protein precipitation sample was prepared by combining one part of blank plasma with 3 parts of acetonitrile (ACN) containing 1% (v/v) formic acid (FA). These samples were vortexed and then centrifuged to remove precipitates. Half the supernatant was spiked, or fortified, with the analytes listed in Table 1. The other half was left blank and spiked with the analyte mixture after passing through the device. An 850 µL, aliquot of the fortified supernatant or 800 µL, of the blank supernatant was added to a 1 cc cartridge containing 30 mg of the synthesized sorbents sandwiched between two polyethylene frits. The extracts were collected at the outlet of the 1 cc cartridges using gravity feed. 50 µL, of the analyte mixture was added to the extracts from the blank plasma samples. The extracts were evaporated under a stream of nitrogen and reconstituted using 200 µL of an 80% methanol in water solution.

For 96-well plate samples assembled using Teflon® frits, the protein precipitation step was performed inside the wells. A purpose of the Teflon frits is to prevent penetration of the bed by the sample until a vacuum of greater than 4" Hg at the exit opening or positive pressure of greater than 4" Hg at the entrance opening is exceeded. The use of Teflon frits is taken as non-limiting examples of porous element having the ability to prevent penetration of the bed by the sample until a vacuum of greater than 4" Hg or positive pressure of greater than 4" Hg is exceeded such as any other sufficiently hydrophobic frit material, membrane, screen or monolithic structure or combination of parts.

Fortified or spiked plasma was prepared by adding a 10× concentration of a mixture of the analytes and diluting it 1:10 with the plasma. 220 µL of the fortified plasma was added to each well followed by the addition of 600 µL of 1% FA in ACN. To wells used as reference standards for recovery, 200 µL of the blank plasma was added to each well followed by the addition of 600 µL of 1% FA in ACN. The sample was mixed by aspirating and dispensing 600 µL of the sample in each well 10 times using an auto-pipette. Wells that were unfilled or not being used were covered with an adhesive backed film before placing the plate on top of a 2 mL 96-well sample collection plate on a vacuum manifold. A vacuum of 15-20" Hg was applied for 5 minutes. To the extracts from the blank plasma wells, 20 µL/well of the analyte mixture was added. The extracts were evaporated under a stream of nitrogen and reconstituted using 200 µL/well of an 80% methanol in water solution.

Mixing in the 96-well plate can be accomplished through vortexing. After adding the precipitating solvent, an unvented cap mat is used to seal the wells. The plate is vortexed for about 1 min then placed on the vacuum manifold over a 2 mL collection plate. A vacuum of 15-20" Hg is applied then released to atmospheric. This sequence is done three times over a five minute period. The release of the vacuum allows the space above the sample to re-equilibrate to atmospheric pressure. This facilitates the emptying of each well by allowing the full available vacuum to be dropped across the slowest draining wells by preventing air loss through the wells that have already emptied. The cap mat may have a diaphragm to increase the space available for expansion under vacuum but should not be vented.

Phospholipid and Analyte Analyses: 2 μL of the reconstituted sample was injected on a 1.8 μm ACQUITY UPLC® HSS T3 column (Waters, Milford Mass.) on an ACQUITY UPLC® System (Waters, Milford Mass.) running the following conditions (Table 2) and gradient method (Table 3):

TABLE 2

| UPLC Column | 1.8 μm, 2.1 × 100 mm ACQUITY UPLC ® HSS T3 |
|---|---|
| Column Temperature | 30° C. |
| PDA Detection | 250-260 nm |
| Injection Volume | 2 μL |
| Run Time | 13 minutes |
| Sampling Rate | 20 (pts/sec) |
| Mobile Phase A1 and A2 | 10 mM pH 3 Ammonia Formate |
| Mobile Phase B1 and B2 | 100% Methanol |
| Strong Needle Wash | Acetonitrile |
| Strong Needle Wash Volume | 500 μL |
| Weak Needle Wash Volume | 1000 μL 10% Methanol |
| Seal Wash | 20/80 acetonitrile/water |
| Injection Loop | 5 μL |
| Injection Option | Partial Loop with Needle Overfill |

TABLE 3

| Time (min) | Flow Rate (mL/min) | % A1 or % A2 | % B1 or % B2 | Transition Curve |
|---|---|---|---|---|
| Initial | 0.42 | 99 | 1 | Initial |
| 7 | 0.42 | 1 | 99 | Linear |
| 12 | 0.42 | 1 | 99 | Linear |
| 12.3 | 0.42 | 99 | 1 | Linear |
| 13 | 0.42 | 99 | 1 | Linear |

The five phospholipids (PL) selected for monitoring belong to the class of phospholipids called glycerophospholipids and in particular the subclass called phosphatidylcholine, all of which contain the trimethylammonium-ethyl phosphate head group (m/z 184). It is widely known in the art that phosphatidylcholines account for 60-70% of all the phospholipids in plasma and are believed to be responsible for the majority of matrix effects. Of the five phosphatidylcholines selected, two are lyso-phosphatidylcholines (m/z 496 and m/z 524), which are the least hydrophobic of the five, due to the lack of a fatty acid ester on the C-2 position.

Using the above chromatographic conditions and gradient, the 9 analytes (eluting between 2.4 and 7.0 min) and 5 phospholipids (eluting between 7.5 and 12 min) are separated from each other to allow for accurate quantitation using two different regions in the gradient. The reconstituted samples and controls were analyzed for the following phospholipids using a Waters Quattro Micro™ Mass Spectrometer (MS) monitoring a single ion recording (SIR) m/z 496→m/z 184, m/z 524→m/z 184, m/z 704→m/z 184, m/z 758→m/z 184, and m/z 806→m/z 184 in electrospray positive (ES+) mode using MassLynx™ MS Software V 4.1. The phospholipids remaining (not retained) in the sample after passing through a sorbent were quantitated relative to those in the plasma supernatant (protein precipitate, ppt) that had not passed through a sorbent. The MS conditions used to analyze for the phospholipids are shown in the table below. Phospholipid results are reported as the % phospholipid retained by the sorbent and are calculated according to the formula below.

$$\% \ PL \ \text{Retained} = \frac{\sum_{i=1}^{5} PL_i^{ppt} - \sum_{i=1}^{5} PL_i^{sorbent}}{\sum_{i=1}^{5} PL_i^{ppt}} * 100$$

where: $PL^{ppt}$ is the total area for the five PL in the sample before passing through the sorbent and $PL^{sorbent}$ is the total area for the five phospholipids remaining in the sample after passing through the sorbent.

TABLE 4

| Parent (m/z) | Daughter (m/z) | Dwell (sec) | Cone (V) | Coll voltage (eV) |
|---|---|---|---|---|
| 184.40 | 184.40 | 0.03 | 90 | 3 |
| 496.40 | 184.40 | 0.03 | 35 | 30 |
| 524.40 | 184.40 | 0.03 | 35 | 30 |
| 704.40 | 184.40 | 0.03 | 35 | 30 |
| 758.40 | 184.40 | 0.03 | 35 | 30 |
| 806.40 | 184.40 | 0.03 | 35 | 30 |

The recoveries were calculated using peak areas from chromatograms obtained using a Waters ACQUITY PDA detector. The % recovery was calculated for each analyte using the following formula: analyte peak areas in the reconstituted fortified samples over the analyte areas in the reconstituted blank samples, spiked with analytes after passing through the sorbent but before evaporation and reconstitution.

Example 1

Porous silica particles (Type A: 20 g of 44 μm irregular particles; SSA=511 m²/g; SPV=0.73 cm³/g; APD=50 Å or Type B: 20 g of 20 μm spherical particles; SSA=338-345 m²/g; SPV=1.04 cm³/g; APD=101 Å) were refluxed in toluene (175 mL, Fisher Scientific, Fairlawn, N.J.) for 1 hour. A Dean-Stark trap was used to remove 75 mL of trace water and toluene from the mixture. Upon cooling, imidazole (Aldrich, Milwaukee, Wis.) and octadecyldimethylchlorosilane (ODMCS, Gelest Inc., Morrisville, Pa.) were added. The reaction was then heated to reflux for 16-18 hours. The reaction was then cooled and the product was filtered and washed successively with toluene, water, and acetone (all solvents from Fisher Scientific). The product was then dried at 70° C. under reduced pressure for 16 hours. A sample of 1b was further refluxed in an acetone/aqueous 0.12 M ammonium acetate solution (Sigma Chemical Co., St. Louis, Mo.) for 2 hours. The reaction was then cooled and the product was filtered and washed successively with water, and acetone (all solvents from Fisher Scientific). The product 1d was then dried at 70° C. under reduced pressure for 16 hours. Reaction and product analysis data are listed in Table 4. The surface coverage of $C_{18}$-groups was determined by the difference in particle % C before and after the surface modification as measured by elemental analysis.

TABLE 5

| Product | Silica Type | Si—OH Concentraion* | ODMCS (g) | Imidazole (g) | Product % C | $C_{18}$ Coverage ($\mu mol/m^2$) |
|---|---|---|---|---|---|---|
| 1a | A | 6.8 | 3.55 | 1.39 | 10.49 | 0.99 |
| 1b | B | 9.2 | 2.35 | 0.92 | 6.99 | 0.95 |
| 1c | B | 8.8 | 2.40 | 0.94 | 6.90 | 0.92 |
| 1d | B | 9.2 | — | — | 6.60 | 0.89 |

*Si—OH concentration ($\mu mol/m^2$) on the particle surface before bonding.

The sorbents from Table 5 were tested with the supernatant of 3:1, 1% FA in ACN:rat plasma, protein precipitation samples, using the procedure described above for 1 cc cartridges. A 3:1 ratio is frequently used to precipitate proteins from plasma samples prior to analysis by LC/MS to prevent fouling LC column inlets with proteins. The addition of the 1% formic acid assists in the recovery of analytes that would interact strongly with residual silanols and/or bind strongly to proteins, thus making the procedure generally applicable (generic). The results of the analyses are shown in Table 6.

TABLE 6

| Product | Silica Type | % PL Retained (n = 7) | Average Analyte (n = 9) % Recovery | Minimum % Recovery | Maximum % Recovery |
|---|---|---|---|---|---|
| 1a | A | 99.9 | 96.1 | 90.3 | 102.8 |
| 1b | B | 98.3 | 94.6 | 89.8 | 96.6 |
| 1c | B | 99.8 | 100.7 | 99.4 | 102.4 |
| 1d | B | 99.5 | 100.0 | 98.1 | 100.7 |

Adequate retention of phospholipids and recovery (pass-through) of analytes were obtained on sorbents 1a-1d. Retention of >95% of the most polar phospholipid and recovery of >70% for all analytes are needed for the successful use of a sorbent in a device designed to remove deleterious levels of phospholipids from protein precipitation samples.

The ratio of the mmol/m² of residual silanols [Si—$OH_{res}$] remaining after bonding to the $\mu mol/m^2$ of $C_{18}$ [$C_{18}$] on the sorbent was calculated using the following formula for monofunctional $C_{18}$ bonded sorbents:

$$\text{Si—OH}_{res}/C_{18}\text{ratio} = \frac{[\text{Si—OH}]_{after\ bonding}}{[C_{18}]} = \frac{[\text{Si—OH}]_{before\ bonding} - [C_{18}]}{[C_{18}]}$$

The calculated Si—$OH_{res}/C_{18}$ ratios for the sorbents in Table 5 ranged from 5.9 to 9.4. This range of Si—$OH_{res}/C_{18}$ ratios has excellent retention for the phospholipids while allowing the diverse set of analytes to pass through the device using protein precipitated samples that contain 75% acetonitrile.

Example 2

Porous silica particles (Type A: 20 g of 44 $\mu m$ irregular particles; SSA=511 $m^2/g$; SPV=0.73 $cm^3/g$; APD=50 Å) were bonded using varying amounts of octadecyldimethylchlorosilane (ODMCS, Gelest Inc., Morrisville, Pa.) to produce a varying amount of ligand on the particle surface. The general procedure described above in Example 1 was used to produce the materials in Table 7. Reaction and product analysis data are listed in Table 7. The surface coverage of $C_{18}$-groups was determined by the difference in particle % C before and after the surface modification as measured by elemental analysis.

TABLE 7

| Product | Silica Type | Si—OH Concentration* | ODMCS (g) | Imidazole (g) | Product % C | $C_{18}$ Coverage ($\mu mol/m^2$) |
|---|---|---|---|---|---|---|
| Silica A | A | 6.8 | none | none | — | 0 |
| 2a | A | 7.9 | 1.50 | 0.59 | 5.2 | 0.54 |
| 2b | A | 7.9 | 3.01 | 1.18 | 7.5 | 0.88 |
| 1a | A | 6.8 | 3.55 | 1.39 | 10.49 | 0.99 |
| 2c | A | 7.9 | 6.0 | 2.36 | 14.9 | 1.77 |
| 2d | A | 7.9 | 9.0 | 3.54 | 18.3 | 2.31 |

*Si—OH concentration ($\mu mol/m^2$) on the particle surface before bonding.

The sorbents from Table 7 were tested with the supernatant of 3:1, 1% FA ACN:rat plasma, protein precipitation samples, using the procedure described above for 1 cc cartridges. The results are shown in Table 8.

TABLE 8

| Product | Si—$OH_{res}$/ $C_{18}$ ratio | % PL Retained Total | % PL Retained m/z 496 | Average Analyte (n = 9) % Recovery | Minimum % Recovery | Maximum % Recovery |
|---|---|---|---|---|---|---|
| Silica A | — | -2.3 | 1.9 | 97.5 | 83.3 | 106.6 |
| 2a | 13.6 | 97.9 | 95.1 | 99.6 | 99.6 | 99.6 |
| 2b | 8.0 | 98.6 | 96.9 | 100.5 | 100.5 | 100.5 |
| 1a | 5.9 | 99.7 | 99.4 | 96.1 | 90.3 | 102.8 |
| 2c | 3.5 | 98.8 | 97.7 | 98.9 | 98.9 | 98.9 |
| 2d | 2.4 | 47.3 | 23.6 | 95.3 | 95.3 | 95.3 |

The data in Table 8 show that all the sorbents listed, including the unbonded silica, give good recoveries for all the analytes in our test mix. The data also show that as the Si—$OH_{res}/C_{18}$ ratio decreases, the sorbent's efficiency for removing phospholipids decreases, especially for the most polar phospholipids, represented in Table 8 by the lyso-phosphotitylcholine (LPC) with m/z 496. Focus is directed at polar phospholipids because these are more likely to elute, on the LC column, in the same region where analytes elute, as mentioned by Little et al. in reversed-phase chromatography [J. Little, M. Wempe, C. Buchanan, J. Chromatogr. B 833 (2006) 219] and Weng et al. in HILIC chromatography [W. Jian, R. W. Edom, Y. g Xu, N. Weng J. Sep. Sci. 2010, 33, 1-17].

There is a very dramatic loss of retention for m/z 496 LPC with Si—OHres/C18 ratios between 3.5 and 2.4, with the most hydrophobic sorbent, 2d, not achieving the desired retention and sorbent 2c still remaining useful for this application. Failure to retain the polar LPC on the most hydrophobic sorbent (2d) indicates that the phospholipotropic characteristic of a sorbent is not solely dependent on retention of the its hydrophobic tail by interaction with the surface C18 chains.

From Table 8, it can further be seen that for high Si—OHres/C18 ratios like 13.6 there are indications that the sorbent (2a) is losing some retention for m/z 496 LPC. It is clear from the data on silica A that the monitored phospholipids are not retained by the silica alone. By rationalizing the phospholipid retention results, obtained on the unbonded silica and the most hydrophobic sorbent (2d), it is not unreasonable to assert that both surface silanols and $C_{18}$ groups are needed for the enhanced retention of the phospholipids required for this invention. Only sorbents containing a particular ratio of Si—$OH_{res}/C_{18}$ are ideal for the removal of phospholipids from protein precipitated plasma/serum samples.

Example 3

Porous silica particles (40 g of 20 μm spherical particles; SSA=338 m²/g; SPV=1.04 cm³/g; APD=101 Å) were refluxed in toluene (275 mL, Fisher Scientific, Fairlawn, N.J.) for 1 hour. A Dean-Stark trap was used to remove 75 mL of trace water and toluene from the mixture. Upon cooling, imidazole (1.8 g, Aldrich, Milwaukee, Wis.) and carbomethoxyethyl trichlorosilane (CMTCS, 3.1 g, Gelest Inc., Morrisville, Pa.) were added. The reaction was then heated to reflux for 19.5 hours. The reaction was then cooled and the product was filtered and washed successively with toluene, water, and acetone (all solvents from Fisher Scientific). The material was then refluxed in an acetone/aqueous 0.12 M ammonium acetate solution (Sigma Chemical Co., St. Louis, Mo.) for 2 hours. The reaction was then cooled and the product was filtered and washed successively with water, and acetone (all solvents from Fisher Scientific). The product 2a was then dried at 70° C. under reduced pressure for 16 hours. Reaction and product analysis data are listed in Table 9. The surface coverage (1.55 μmol/m²) was determined by the difference in particle % C before and after the ODMCS surface modification as measured by elemental analysis.

A sample of this material (10 g) was refluxed in toluene (275 mL, Fisher Scientific, Fairlawn, N.J.) for 1 hour. A Dean-Stark trap was used to remove 75 mL of trace water and toluene from the mixture. Upon cooling, imidazole (0.46 g, Aldrich, Milwaukee, Wis.) and octadecyldimethylchlorosilane (1.2 g, ODMCS, Gelest Inc., Morrisville, Pa.) were added. The reaction was then heated to reflux for 4 hours. The reaction was then cooled and the product was filtered and washed successively with toluene, water, and acetone (all solvents from Fisher Scientific). Product 2b was then dried at 70° C. under reduced pressure for 16 hours. Reaction and product analysis data are listed in Table 9. Additional surface coverage due to $C_{18}$-groups (0.86 mmol/m²) was determined by the difference in particle % C before and after the ODMCS surface modification as measured by elemental analysis.

TABLE 9

| Product | Precursor | Si—OH Concentration* | Silane | % C | Coverage (μmol/m²) |
|---|---|---|---|---|---|
| Silica B | — | 8.8 | — | 0 | — |
| 3a | Silica B | 9.2 | CMTCS | 2.34 | 1.55 CBA + ester<sup>a</sup> |
| 3b | 3a | 9.2 | ODMCS | 8.12 | 0.86 C18 |
| 1d | Silica B | 9.2 | ODMCS | 6.60 | 0.89 C18 |
| 3c | 1d | 9.2 | HMDS | 8.10 | 1.52 TMS |

*Si—OH concentration (μmol/m²) on the particle surface before bonding. <sup>a</sup>Carboxylic acid and its ester The sorbents from Table 9 were tested with the supernatant of 3:1, 1% FA ACN:rat plasma, protein precipitation samples, using the procedure described above for 1 cc cartridges. The results are shown in Table 10.

TABLE 10

| Product | Precursor | % PL Removed | Average Analyte % Recovery | Minimum % Recovery | Maximum % Recovery |
|---|---|---|---|---|---|
| Silica B | — | 0 | 98.6 | 94.6 | 104.0 |
| 3a | Silica B | 16.1 | 93.0 | 87.8 | 94.6 |
| 3b | 3a | 98.7 | 97.8 | 95.4 | 109.0 |
| 1d | Silica B | 99.5 | 100.0 | 98.1 | 100.7 |
| 3c | 1d | 55.9 | 94.3 | 84.6 | 97.4 |

The unbonded silica B and all the bonded sorbents in Table 10 provide good recoveries for the all analytes. Silica B and sorbent 3a did not adequately retain the phospholipids due to the lack of the hydrophobic $C_{18}$ groups. The presence of the carboxylic acid and/or its ester in addition to $C_{18}$ on sorbent 3b was not detrimental to the retention of the phospholipids, acting similarly to the silanol groups replaced by the CBA+ester groups. Unlike sorbent 3b, the presence of the trimethyl silyl (TMS) endcap group in addition to the $C_{18}$ group on sorbent 3c was detrimental to the retention of phospholipids, indicating that the TMS group is disrupting access to the needed silanol groups for the 2-group interaction which results in the enhanced retention for phospholipids.

The data indicate that the carboxylic acid, and/or its ester, maintains the phospholipotropic characteristic of the sorbent 3b while the presence of the trimethyl silyl group on sorbent 3c does not. It is important to point out that the total coverages on both sorbents 3b and 3c are 2.41 mmol/m² and, both have 0.9 mmol/m² $C_{18}$ on the surface but only one of the sorbents maintains adequate retention for phospholipids. Both of these sorbents have a Si—$OH_{res}/C_{18}$ ratio of about 7.8, which has previously fallen into the acceptable range. Because the carboxylic acid, and/or its ester, appears to provide a polar group similar to those provided by silanols, sorbent 3b maintains its PL retention. However, the sorbent 3c, because of the lack of phospholipotropic characteristic, behaves as a sorbent with a Si—$OH_{res}/C_{18}$ ratio of 2.8 (see Table 11 below), which falls clearly into the ratio range in which PL retention is not optimal.

Phospholipid affinity toward silanol and $C_{18}$ groups is not unique only to these groups, the above data can be tabulated assuming the TMS groups add to the hydrophobic group concentration. The ratios in Table 11 were expressed as the combined coverages for polar groups, which in this case is [Si—$OH_{res}$+CBA and ester], over the combined coverages of hydrophobic groups, which in this case is [C18+TMS]. Based on the % PL retained data, the ratios for all sorbents in Table 11 are now inline with products made using only C18 groups on silica. In total, the data indicates that any number of combinations of polar groups with any number of combinations of hydrophobic groups, can be taken together as the 2-group interaction required for enhanced retention of phospholipids.

TABLE 11

| Product | Coverage of Hydrophobic groups μmol/m² | | Coverage of Polar Groups μmol/m² | | [Polar]/[Hydrophobic] Ratio | % PL Retained |
|---|---|---|---|---|---|---|
| | C18 | TMS | CBA + ester | SiOH$_{res}$ | | |
| 1d | 0.89 | — | — | 8.31 | 9.3 | 99.5 |
| 3c | 0.89 | 1.52 | — | 6.79 | 2.8 | 55.9 |
| 2d | 2.30 | — | — | 5.60 | 2.4 | 47.3 |
| 3b | 0.86 | — | 1.55 | 8.36 | 9.7 | 98.7 |

Example 4

The general procedure described in 1 can be applied to a variety of different porous materials. Included in this are monolithic, spherical, granular, superficially porous, and irregular materials that are inorganic (silica, alumina, titania, zirconia) or hybrid inorganic/organic materials. Also included in this are materials that independently have an inorganic (silica, alumina, titania, zirconia) or hybrid inorganic/organic materials surface layer on a porous inorganic (silica, alumina, titania, zirconia) or hybrid inorganic/organic materials core material. The particles size for spherical, granular or irregular materials can vary from 1-500 μm; more preferably 1-60 μm; more preferably 15-30 μm. The APD for these materials can vary from 30 to 2,000 Å; more preferably 40 to 200 Å; more preferably 45 to 160 Å. The SSA for these materials can vary from 20 to 1000 m²/g; more preferably 90 to 800 m²/g; more preferably 150 to 600 m²/g; more preferably 200 to 550 m²/g. The TPV for these materials can vary from 0.3 to 1.7 cm³/g; more preferably 0.5 to 1.2 cm³/g; more preferably 0.7 to 1.1 cm³/g. The macropore diameter for monolithic materials can vary from 0.1 to 30 μm, more preferably 0.5 to 25 μm, more preferably 1 to 20 μm.

Surface modifiers used for these reactions include silanes having formula (II)

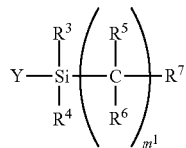

(II)

or the formula (III):

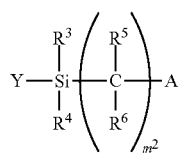

(III)

or a combination thereof, wherein
$m^1$ is an integer from 5-30, more preferably 8-30, more preferably 12-30, more preferably 18;
$m^2$ is an integer from 0-30, more preferably 0-18, more preferably 0-6;
each occurrence of $R^3$ and $R^4$ independently represents —OH, hydrogen, methyl, ethyl, n-butyl, iso-butyl, tert-butyl, iso-propyl, thexyl, substituted or unsubstituted aryl, cyclic alkyl, branched alkyl, lower alkyl, or group Y;

each occurrence of $R^5$ and $R^6$ independently represents hydrogen, methyl, ethyl, n-butyl, t-butyl, i-propyl, lower alkyl, or group A;

$R^7$ independently represents hydrogen, alkyl, alkenyl, alkynyl, substituted or unsubstituted aryl, cyano, amino, diol, nitro, nitrophenyl, a cation or anion exchange group, zwitterionic group, a monocyclic or bicyclic heterocyclic or heteroaryl ring system, or a chiral moiety;

Y represents —H, —OH, —OR$^8$, —NR$^8$, —OSO$_2$CF$_3$, or —Cl; where R$^8$ represents hydrogen, methyl, ethyl, n-butyl, iso-butyl, tert-butyl, iso-propyl, thexyl, phenyl, branched alkyl or lower alkyl;

A represents the protected, protonated or salt form of an alkyl or aryl cation exchange group including a carboxylic acid group, phenol, imide, sulfonic acid, boronic, phosphonic acid, or —R$^9$R$^{10}$SiOH where R$^9$ and R$^{10}$ independently represent methyl, ethyl, n-butyl, t-butyl, i-propyl or lower alkyl; and When $m^2$=0, A represents the organic group protected, protonated or salt form of a an alkyl or aryl cation exchange group including a carboxylic acid group, phenol, or —OH.

Protecting groups for cation exchange groups can vary, as described in Protective Groups in Organic Synthesis [T. W. Green and P. G. M. Wuts, John Wiley & Sons, Inc, 1999].

Porous materials are dried in refluxing toluene for a minimum of 1 hour using a Dean-Stark trap. Upon cooling, imidazole and the surface modifier(s) are added. Reactions using a mixture of surface modifiers can range from a 1:99 to 99:1 ratio of surface modifiers I/II. Reactions using more than one type of surface modifier I and/or more than one type of surface modifier II have the ratio of type I-sum (defined as I$^a$+I$^b$ . . . I$^i$) to type II-sum (defined as II$^a$+II$^b$ . . . II$j$) range from 1:99 to 99:1 ratio of surface modifiers I-sum/II-sum.

The reaction is heated to reflux in toluene for 16-18 hours. The reaction is cooled and the product is filtered and washed successively with toluene, water, and acetone. A hydrolysis can be performed for 2-20 hours at 50° C., using an aqueous acetone solution that is pH controlled between pH 2-10. The reaction is cooled and the product is filtered and washed successively with toluene, water, and acetone.

The product is then dried at 70° C. under reduced pressure for 16 hours. The resulting surface coverage is determined by the difference in particle % C before and after the surface modification as measured by elemental analysis. The surface coverage obtained by this approach ranges from 0.4 to 3.2 μmol/m²; more preferably 0.5 to 2.7 μmol/m², more preferably 0.6 to 2.2 μmol/m².

| | Coverage of polar groups / Coverage of hydrophobic groups |
|---|---|
| preferred | 1.5-26 |
| more preferred | 2.0-18 |
| most preferred | 3.5-14 |

Example 5

The general procedure described in 1 was used to prepare the sorbent in this example.

A 96-well plate was assembled using 1.5 mm thick Teflon® frits having a nominal pore size of 10 μm at the bottom of the wells, 25 mg of the sorbent 5a described below, and 1.0 mm thick Teflon® top frits having a nominal pore size of 10 μm. The Teflon® frits permit loading and mixing of both the plasma and 1% FA in ACN solutions in each well, without loss of sample by leaking at the well outlet tips. Delay times as long as 1 hour, prior to evacuating the wells by vacuum, showed no signs of leaking at the well outlet tips. In addition, the plates were vortexed for up to 3 min without loss of sample due to leaking. Unlike in previous examples, the protein precipitation steps are performed in the plate. Details of the procedure are given above. 220 μL, of spiked rat plasma followed by 600 μL of 1% FA in ACN was added to each of 4 wells. To another set of 4 wells, 200 μL, of blank rat plasma followed by 600 μL, of 1% FA in ACN was added. The content of each well was aspirated 10× using a volume of 600 μm, to mix the samples. An adhesive film was used to cover the unfilled or unused wells in the plate. The plate was placed over a 2 mL 96-well sample collection plate on a vacuum manifold. A vacuum of 15-20" Hg was applied for 5 minutes. All wells emptied within this time and the sample extracts were visibly clear. 20 μL of the analyte mixture used to fortify the rat plasma, were added to each well of the extracts from the blank rat plasma. These post extraction spiked wells are used to establish the degree of recovery for the spiked rat plasma samples wherein the analytes passed through the sorbent. All extracts were dried under a stream of nitrogen with the plate at 50° C. until all samples were evaporated.

TABLE 12

| Product | Silica Type | Si—OH Concentration* | ODMCS (g) | Imidazole (g) | Product % C | $C_{18}$ Coverage (μmol/m²) |
|---|---|---|---|---|---|---|
| 5a | B | 9.2 | 2.35 | 0.92 | 6.95 | 0.94 |

*Si—OH concentration (μmol/m²) on the particle surface before bonding.

TABLE 13

| Product | Silica Type | % PL Retained (n = 7) | Average Analyte (n = 9) % Recovery | Minimum % Recovery | Maximum % Recovery |
|---|---|---|---|---|---|
| 5a | B | 100 | 87.3 | 81.6 | 91.5 |

One advantage of this plate configuration is that the plate can be used to perform high throughput protein precipitation. The method presented in this example demonstrates efficiency gains with in-well protein precipitation by avoiding the sample transfer, vortexing, and centrifugation steps needed prior to loading the sample supernatant on the sorbent using standard frits. In contrast, the plasma pipetted into the plate followed by the addition of the of the 1% FA in ACN precipitating solvent is mixed by aspiration and eluted into a sample collection plate using vacuum or positive pressure. Samples can be analyzed as is or evaporated and reconstituted in a smaller volume for increased sensitivity. This protocol is completely compatible with commercially available robotic systems.

Example 6

The general procedure described in 1 can be applied to a variety of different porous materials. Included in this are monolithic, spherical, granular, and irregular materials that are silica or hybrid inorganic/organic materials, as described in Example 4.

Porous materials, as described in Example 4, are dried in refluxing toluene for a minimum of 1 hour using a Dean-Stark trap. Upon cooling, imidazole and surface modifier II, as described in Example 4, are added. The reaction is heated to reflux in toluene for 16-18 hours. The reaction is cooled and the product is filtered and washed successively with toluene, water, and acetone. A hydrolysis can be performed for 2-20 hours at 50° C., using an aqueous acetone solution that is pH controlled between pH 2-10. The product is then dried at 70° C. under reduced pressure for 16 hours. Alternatively, the material can be used without drying. The resulting surface coverage of dried material is determined by the difference in particle % C before and after the surface modification as measured by elemental analysis. The surface coverage obtained by this approach ranges from 0.5 to 3.2 μmol/m²; more preferably 0.6 to 2.7 μmol/m², more preferably 0.8 to 2.2 μmol/m².

These materials are further dried in refluxing toluene for a minimum of 1 hour using a Dean-Stark trap. Upon cooling, imidazole and surface modifier I, as described in Example 3, are added. The reaction is heated to reflux in toluene for 16-18 hours. The reaction is cooled and the product is filtered and washed successively with toluene, water, and acetone. A hydrolysis can be performed for 2-20 hours at 50° C., using an aqueous acetone solution that is pH controlled between pH 2-10. The product is then dried at 70° C. under reduced pressure for 16 hours. The resulting surface coverage is determined by the difference in particle % C before and after the surface modification as measured by elemental analysis. The surface coverage obtained by this approach ranges from 0.5 to 3.2 μmol/m²; more preferably 0.6 to 2.7 μmol/m², more preferably 0.8 to 2.2 μmol/m².

Example 7

The general procedure described in Example 1 can be applied to a variety of different porous materials. Included in this are monolithic, spherical, granular, and irregular materials that are silica or hybrid inorganic/organic materials, as described in Example 4.

Porous materials, as described in Example 4, are dried in refluxing toluene for a minimum of 1 hour using a Dean-Stark trap. Upon cooling, imidazole and surface modifier I, as described in Example 4, are added. The reaction is heated to reflux in toluene for 16-18 hours. The reaction is cooled and the product is filtered and washed successively with toluene, water, and acetone. A hydrolysis can be performed for 2-20 hours at 50° C., using an aqueous acetone solution that is pH controlled between pH 2-10. The product is then dried at 70° C. under reduced pressure for 16 hours. Alternatively, the material can be used without drying. The resulting surface coverage of dried material is determined by the difference in particle % C before and after the surface modification as measured by elemental analysis. The surface coverage obtained by this approach ranges from 0.5 to 3.2 µmol/m$^2$; more preferably 0.6 to 2.7 µmol/m$^2$, more preferably 0.8 to 2.2 µmol/m$^2$.

These materials are further dried in refluxing toluene for a minimum of 1 hour using a Dean-Stark trap. Upon cooling, imidazole and surface modifier II, as described in Example 3, are added. The reaction is heated to reflux in toluene for 16-18 hours. The reaction is cooled and the product is filtered and washed successively with toluene, water, and acetone. A hydrolysis can be performed for 2-20 hours at 50° C., using an aqueous acetone solution that is pH controlled between pH 2-10. The product is then dried at 70° C. under reduced pressure for 16 hours. The resulting surface coverage is determined by the difference in particle % C before and after the surface modification as measured by elemental analysis. The surface coverage obtained by this approach ranges from 0.5 to 3.2 µmol/m$^2$; more preferably 0.6 to 2.7 µmol/m$^2$, more preferably 0.8 to 2.2 µmol/m$^2$.

Example 8

Spherical 20 µm (Type B) porous silica particles (60 g, Daiso Corporation, Osaka, Japan; 0% C; SSA=345 m$^2$/g; SPV=1.03 cm$^3$/g; APD=99 Å) of the formula SiO$_2$ were coated with zirconia by the method described in US Patent Application US 2008/0212906A1, Example 1 using zirconium propoxide purchased from Gelest Inc., Morrisville, Pa.

The specific surface area of the zirconia coated silica was measured to be 325 m$^2$/g. The zirconium content of the zirconia coated silica was found to be 2.9% by ICP-AE. The carbon content of the zirconia coated silica was determined to be 2.3%.

30 grams of the zirconia coated silica were refluxed in toluene (250 mL, Fisher Scientific, Fairlawn, N.J.) for 1.5 hours. A Dean-Stark trap was used to remove 100 mL of trace water and toluene from the mixture. Upon cooling, 1.33 grams of imidazole (Aldrich, Milwaukee, Wis.) and 3.38 grams of octadecyldimethylchlorosilane (Gelest Inc., Morrisville, Pa.) were added. The reaction was then heated to reflux for 4 hours. The reaction was then cooled and the product was filtered and washed successively with toluene, acetone, 1:1 v/v acetone/water and acetone (all solvents from Fisher Scientific). The product was then dried at 70° C. under reduced pressure for 16 hours.

The carbon content of the zirconia coated silica after octadecyldimethylchlorosilane bonding was determined to be 8.3%. The octadecyldimethylsilane surface coverage was determined to be 0.84 µmol/m$^2$.

TABLE 14

| Product | Silica Type | —OH Concentration* | ODMCS (g) | Imidazole (g) | Product % | Coverage (µmol/m$^2$) |
|---|---|---|---|---|---|---|
| 6a | B | 14.6 | — | — | 2.9% Zr | 0.98 Zr |
| 6b | 6a | 13.8 | 3.38 | 1.33 | 8.3% C | 0.84 C$_{18}$ |

*The hydroxyl concentration (µmol/m$^2$) on the particle surface before bonding.

TABLE 15

| Product | Precursor | % PL Removed | Average Analyte % Recovery | Minimum % Recovery | Maximum % Recovery |
|---|---|---|---|---|---|
| 6a | B | 83.4 | 82.0 | 75.6 | 86.0 |
| 6b | 6a | 100 | 79.6 | 60.0 | 100 |
| 5a | B | 100 | 87.3 | 81.6 | 91.5 |

The data in Table 15 was generated using the same 96-well plate configuration and protocol as described in example 5. Unlike silica, zirconia is known to have an affinity for phospholipids, which is demonstrated by the 83.4% removal of the phospholipids on 6a. In addition, the data indicates that the phospholipid removal efficiency was improved on the zirconia coated silica (6a) when 0.84 µmol/m$^2$ of C18 is added to the sorbent (6b). The addition of C18 to the zirconia coated silica did not adversely affect the recovery of the analytes. Although equivalent amounts of phospholipids were removed on the C18 bonded zirconia coated silica (6b) and the C18 bonded silica (5a), the average recovery on the C18 bonded silica (5a) was higher, presumed to be due to the absence of Lewis-acid Lewis-base interactions that interfere with the recovery on the zirconia coated media (6a and 6b).

Example 9

Irregular 40 µm porous silica particles (20 g, Daiso Corporation, Osaka, Japan; 0% C; SSA=433 m$^2$/g; SPV=0.69 cm$^3$/g; APD=52 Å) of the formula SiO$_2$ were refluxed in toluene (175 mL, Fisher Scientific, Fairlawn, N.J.) for 1 hour. A Dean-Stark trap was used to remove 75 mL of trace water and toluene from the mixture. Upon cooling, 1.18 grams of imidazole (Aldrich, Milwaukee, Wis.) and 1.79 grams of octyldimethylchlorosilane (Gelest Inc., Morrisville, Pa.) were added. The reaction was then heated to reflux for 4 hours. The reaction was then cooled and the product was filtered and washed successively with toluene, acetone, 1:1 v/v acetone/water and acetone (all solvents from Fisher Scientific). The product was then dried at 70° C. under reduced pressure for 16 hours. Reaction and product analysis data are listed in Table 16.

Irregular 40 µm porous silica particles (100 g, Daiso Corporation, Osaka, Japan; 0% C; SSA=433 m$^2$/g; SPV=0.69 cm$^3$/g; APD=52 Å) of the formula SiO$_2$ were refluxed in toluene (600 mL, Fisher Scientific, Fairlawn, N.J.) for 1 hour. A Dean-Stark trap was used to remove 100 mL of trace water and toluene from the mixture. Upon cooling, 5.9 grams of imidazole (Aldrich, Milwaukee, Wis.) and 15.0 grams of octadecyldimethylchlorosilane (Gelest Inc., Morrisville, Pa.) were added. The reaction was then heated to reflux for 4 hours. The reaction was then cooled and the product was filtered and washed successively with toluene, acetone, 1:1 v/v acetone/water and acetone (all solvents from Fisher Scientific). The product was then dried at 70° C. under reduced pressure for 16 hours. Reaction and product analysis data are listed in Table 16.

TABLE 16

| Product | Silica Type | Si—OH Concentration* | Silane (g) | Imidazole (g) | Product % | Coverage (µmol/m$^2$) |
|---|---|---|---|---|---|---|
| 7a | A | 7.9 | 1.79 | 1.18 | 5.34% C | 1.1 C$_8$ |
| 7b | A | 7.9 | 15.0 | 5.9 | 8.97% C | 0.98 C$_{18}$ |

*Si—OH concentration (µmol/m$^2$) on the particle surface before bonding.

TABLE 17

| Product | Precursor | Ratio $\frac{[Si-OH]_{res}}{[C_{18}] \text{ or } [C_8]}$ | % PL Retained total | % PL Retained m/z 496 | Average Analyte % Recovery |
|---|---|---|---|---|---|
| 7a | A | 6.2 | 63 | 56 | 93.0 |
| 7b | A | 7.1 | 100 | 94 | 80.4 |

As shown in Table 17, PL removal efficiency of C8 and C18 is not equivalent. The hydrophobicity of the C8 is less than that of C18 and does not achieve the desired performance for this particular application, even though its ratio is within the range of those for acceptable C18 materials.

Example 10

Due to the lack of an insufficiently low coverage C18 bonded material, a plot of the % phospholipid removed versus the ratios for the presented data can not describe a narrow region where enhance retention of phospholipids for this application is observed. However, a plot of the reciprocal can make use of the unbonded silica (ratio=infinity; 1/ratio=0) to make this point. Because the most polar of the phospholipids (lyso-phosphatidylcholines) is most likely to interfere with the chromatographic analyses of small molecules, its removal is most critical and will be used to demonstrate the desired ratio range.

Figure 4:
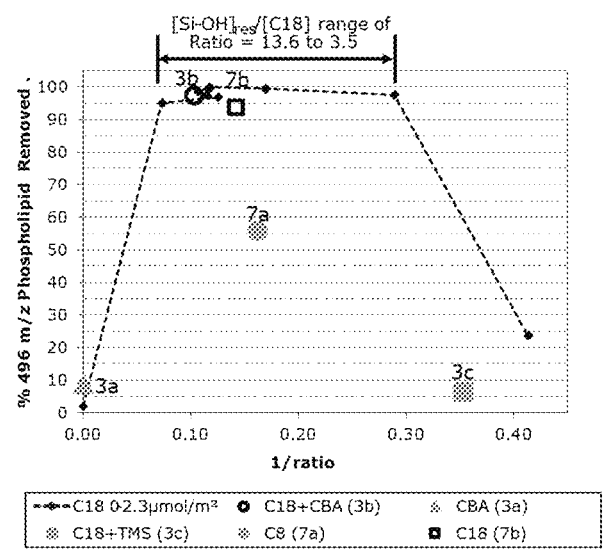
FIG. 4 depicts a plot of the % removal of the phospholipid having an m/z of 496 versus the reciprocal of the ratio of the residual silanols to the C18 surface concentrations.

FIG. 4 depicts plot of the % removal of the phospholipid having an m/z of 496 versus the reciprocal of the ratio of the residual silanols to the C18 surface concentrations. The region in the graph where the removal exceeds 90% is equivalent to ratios of 13.6 to 3.5. Ratios higher than 13.6 and lower than 3.5 may produce better than 90% removal of the 496 m/z phospholipid and therefore would be acceptable, at least in this example. Added to this plot of FIG. 4 are points from all the previously presented data on silica. A comprehensive set of data for the materials in the plot of FIG. 4 are presented in Table 18.

The sorbents that define the curve for C18 coverages between 0 and 2.3 μmol/m² demonstrate the effect of varying the ratio of silanol to C18 interactions on the efficacy of removal/retention of the most polar phospholipid, lyso-phosphatidylcholines. A clear region is defined where acceptable performance is achieved.

Other points have been added to the plot that show acceptable performance such as that for sorbent 3b where the CBA groups act as polar groups. Coverage of the CBA groups alone, assuming equivalency to C18, would have produced a ratio of 4.9 (1/ratio=0.20), and had they been sufficiently hydrophobic, would have predicted acceptable removal of the lyso-phosphatidylcholines, but as expected did not give the desired results in this case.

The data for 7a and 7b indicate that the desired performance for the sorbent in this invention is also not achieved by use of the C8 bonded silica. The same silica bonded with C18 to essentially the same coverage provides the needed retention for the phospholipids. The difference here is that the C8 groups are insufficiently hydrophobic and although the retentivity of the sorbent could be increased by increasing the coverage for the C8 sorbent, this would be done at the loss of the necessary silanol groups in this case.

TABLE 18

| Product | TGA Si—OH* | Hydrophobic Interactions Coverage** | Hydrophobic Interactions Groups | Polar Interactions Coverage** | Polar Interactions Groups | Ratio*** | 1/Ratio | % PL Removed Total | % PL Removed 496 m/z |
|---|---|---|---|---|---|---|---|---|---|
| Silica A | 6.8 | 0.00 | none | 6.8 | Si—OH | infinite | 0 | −2 | 2 |
| 2a | 7.9 | 0.54 | C18 | 7.36 | Si—OH | 13.6 | 0.07 | 98 | 95 |
| 2b | 7.9 | 0.88 | C18 | 7.02 | Si—OH | 8.0 | 0.13 | 99 | 97 |
| 1d | 9.2 | 0.89 | C18 | 8.35 | Si—OH | 9.4 | 0.11 | 100 | 99 |
| 1c | 8.8 | 0.92 | C18 | 7.86 | Si—OH | 8.5 | 0.12 | 100 | 100 |
| 1b | 9.2 | 0.95 | C18 | 8.29 | Si—OH | 8.7 | 0.11 | 98 | 98 |
| 5a | 9.2 | 0.97 | C18 | 8.22 | Si—OH | 8.5 | 0.12 | 100 | 100 |
| 1a | 6.8 | 0.99 | C18 | 5.83 | Si—OH | 5.9 | 0.17 | 100 | 99 |
| 2c | 7.9 | 1.77 | C18 | 6.13 | Si—OH | 3.5 | 0.29 | 99 | 98 |
| 2d | 7.9 | 2.31 | C18 | 5.59 | Si—OH | 2.4 | 0.41 | 47 | 24 |
| 3c | 9.2 | 2.41 | C18 + TMS | 6.83 | Si—OH | 2.8 | 0.35 | 56 | 6 |
| 3b | 9.2 | 0.86 | C18 | 8.36 | Si—OH + CBA + ester | 9.7 | 0.10 | 99 | 97 |
| 7a | 7.9 | 1.10 | C8 | 6.80 | Si—OH | 6.2 | 0.16 | 63 | 56 |
| 7b | 7.9 | 0.98 | C18 | 6.92 | Si—OH | 7.1 | 0.14 | 100 | 94 |
| 3a | 9.2 | 0.98 | none | 8.24 | Si—OH + CBA + ester | infinite | 0 | 16 | 9 |

*Si—OH concentration (μmol/m²) on the particle surface before bonding.
**Coverage in μmol/m²
***Ratio = [polar groups]/[hydrophobic groups]

The invention claimed is:

1. An apparatus for separating a liquid sample comprising proteins, phospholipids, and small molecules, the apparatus comprising:
   a housing having at least one wall defining one or more chambers, each chamber having
   (i) an exit opening and an entrance opening;
   (ii) a wetting barrier having a first plurality of openings and formed of a fluorocarbon polymer, the wetting barrier disposed between the exit opening and the entrance opening, so as to define a separation media space between the wetting barrier and the exit opening and a sample receiving space between the wetting barrier and the entrance opening;
(iii) a sorbent disposed in the separation media space, the sorbent having a core composition and a surface composition represented by Formula I:

W-[X]-Q        Formula I wherein
X represents the core composition;
W and Q occupy free valences of the core or surface composition that are not X;
W is a hydroxyl group;
Q is an aliphatic silane group wherein the aliphatic silane group comprises 6 to 30 carbons,
wherein W and Q form the surface composition, and the surface coverage of Q is between 0.4 to 3.2 $\mu mol/m^2$; and
(iv) at least one frit disposed between the wetting barrier and the entrance opening, the at least one frit having a second plurality of openings, the second plurality of openings larger than the first plurality of openings of the wetting barrier,
wherein the wetting barrier is adapted to (a) retain the liquid sample and a protein precipitating agent in the sample receiving area to mix the liquid sample and the protein precipitating agent, thereby facilitating the formation of a protein precipitate and a processed sample; and (b) flow the processed sample through the wetting barrier and sorbent, thereby retaining the protein precipitate in the sample receiving area, retaining phospholipids in the separation media space, and eluting small molecules.

2. The apparatus of claim 1, wherein the wetting barrier is a frit.

3. The apparatus of claim 1, wherein the fluorocarbon polymer is polytetrafluoroethylene.

4. The apparatus of claim 1, wherein the aliphatic silane group comprises 18 carbons.

5. The apparatus of claim 1, wherein the surface coverage of Q is between 0.5 to 2.7 $\mu mol/m^2$.

6. The apparatus of claim 1, wherein the surface coverage of Q is between 0.6 to 2.2 $\mu mol/m^2$.

7. The apparatus of claim 1, wherein the surface coverage of Q is between 0.5 to 1.8 $\mu mol/m^2$.

8. The apparatus of claim 1, wherein the processed sample is flowed through the wetting barrier and sorbent by the application of a vacuum or positive pressure that is greater than 4 inches of mercury.

9. The apparatus of claim 1, wherein the processed sample is flowed through the wetting barrier and sorbent by centrifugal force.

10. The apparatus of claim 1, wherein the sorbent has a specific affinity for phospholipids.

11. The apparatus of claim 1, wherein a ratio of W to Q is between 3.5 and 13.6.

12. The apparatus of claim 1, wherein the housing has a plurality of chambers.

13. The apparatus of claim 12, wherein the housing is constructed and arranged to present 8 chambers or multiples of 8 chambers.

14. The apparatus of claim 12, wherein the housing is constructed and arranged to present 96 chambers.

15. A method for separating a liquid sample comprising proteins, phospholipids, and small molecules, the method comprising:
(a) providing a housing having at least one wall defining one or more chambers, each chamber having
(i) an exit opening and an entrance opening;
(ii) a wetting barrier having a first plurality of openings and formed of a fluorocarbon polymer, the wetting barrier disposed between the exit opening and the entrance opening, so as to define a separation media space between the wetting barrier and the exit opening and a sample receiving space between the wetting barrier and the entrance opening;
(iii) a sorbent disposed in the separation media space, the sorbent having a core composition and a surface composition represented by Formula I:

W-[X]-Q        Formula I wherein
X represents the core composition;
W and Q occupy free valences of the core or surface composition that are not X;
W is a hydroxyl group;
Q is an aliphatic silane group wherein the aliphatic silane group comprises 6 to 30 carbons,
wherein W and Q form the surface composition, and the surface coverage of Q is between 0.4 to 3.2 $\mu mol/m^2$; and
(iv) at least one frit disposed between the wetting barrier and the entrance opening, the at least one frit having a second plurality of openings, the second plurality of openings larger than the first plurality of openings of the wetting barrier;
(b) combining the liquid sample and a protein precipitating agent in the sample receiving area;
(c) mixing the combined liquid sample and protein precipitating agent to form a protein precipitate and a processed sample;
(d) flowing the processed sample through the wetting barrier and sorbent, thereby retaining at least a fraction of the protein precipitate in the sample receiving area, retaining phospholipids in sorbent, and eluting small molecules.

16. The method of claim 15, wherein the protein precipitating agent is acetonitrile.

17. The method of claim 15, wherein the protein precipitating agent comprises acetonitrile and 1% (v/v) formic acid.

18. The method of claim 15, wherein the mixing is accomplished through vortexing.

19. The method of claim 15, wherein the flowing is accomplished by the application of a positive pressure that is greater than 4 inches of mercury.

20. The method of claim 15, wherein the flowing is accomplished by the application of a centrifugal force.

21. The method of claim 16, wherein a ratio of W to Q is between 3.5 and 13.6.

22. The method of claim 16, wherein the fluorocarbon polymer is polytetrafluoroethylene.

* * * * *